(12) United States Patent
Bessette et al.

(10) Patent No.: US 6,841,577 B2
(45) Date of Patent: Jan. 11, 2005

(54) PESTICIDAL ACTIVITY OF PLANT ESSENTIAL OILS AND THEIR CONSTITUENTS

(75) Inventors: Steven M. Bessette, Brentwood, TN (US); Myron A. Beigler, Santa Rosa, CA (US)

(73) Assignee: Ecosmart Technologies, Inc., Roswell, GA (US)

( * ) Notice: Subject to any disclaimer, the term of this patent is extended or adjusted under 35 U.S.C. 154(b) by 44 days.

(21) Appl. No.: 10/023,145

(22) Filed: Dec. 18, 2001

(65) Prior Publication Data

US 2002/0107287 A1 Aug. 8, 2002

Related U.S. Application Data

(63) Continuation-in-part of application No. 09/302,198, filed on Apr. 29, 1999, now abandoned.

(51) Int. Cl.[7] .......................... A01N 31/14; A01N 27/00
(52) U.S. Cl. ....................... 514/720; 514/731; 514/733; 514/762; 424/405; 424/406
(58) Field of Search ................................ 424/405, 406, 424/409, 417, 421; 514/720, 731, 733, 762

(56) References Cited

U.S. PATENT DOCUMENTS

| | | | |
|---|---|---|---|
| 4,219,570 A | 8/1980 | Inazuka et al. | 424/343 |
| 4,933,371 A | 6/1990 | Hink et al. | 514/739 |
| 5,030,659 A | 7/1991 | Bansemir et al. | 514/635 |
| 5,110,594 A | 5/1992 | Morita | 424/405 |
| 5,118,506 A | 6/1992 | Eichoefer | 424/196.1 |
| 5,439,690 A | 8/1995 | Knight | 424/687 |
| 5,653,991 A | 8/1997 | Rod | 424/406 |
| 5,676,958 A | 10/1997 | Emerson et al. | 424/405 |
| 5,900,244 A | 5/1999 | Howse | 424/405 |
| 6,114,384 A * | 9/2000 | Bessette et al. | 514/546 |
| 6,531,163 B1 * | 3/2003 | Bessette et al. | 424/747 |
| 6,534,099 B1 * | 3/2003 | Bessette et al. | 424/757 |

FOREIGN PATENT DOCUMENTS

DE   42 31 045 A 1   3/1994

OTHER PUBLICATIONS

James A. Nathanson and Edward J. Hunnicutt, "N–Demethylchlordimeform a Potent Partial Agonist of Octopamine–Sensitive Adenylate Cyclase"; Molecular Pharmacology, 20:68–75; Feb. 5, 1981.

James A. Nathanson, "Phenyliminoimidazolidizines Characterization of a Class of Potent Agonists of Octopamine–Sensitive Adenylate Cyclase and Their use in Understanding the Pharmacology of Octopamine Recceptors"; Molecular Pharmacology, 28:254–268: Jun. 5, 1985.

Joel M. Wierenga and Robert M. Hollingworth, "Octopamine Uptake and Metabolism in the Insect Nervous System"; Journal of Neurochemistry; Jun. 29, 1989; pp. 479–489.

A. Guillen et al, "A possible new class of octopamine receptors coupled to adenylate cyclase in the brain of the dipterous *Ceratitis capitata*. Pharmacological characterization and regulation of 3H–octopamine binding", Life Sci., vol. 45, No. 7, 1989, pp. 655–662.

(List continued on next page.)

*Primary Examiner*—Neil S. Levy
(74) *Attorney, Agent, or Firm*—Armstrong, Kratz, Quintos, Hanson & Brooks, LLP (57) ABSTRACT

A pesticide for cockroaches and larvae which is based on purified naturally occurring plant substances. Phenethyl propionate; methyl salicylate; pulegone; carvacrol; thymol; thyme oil; citronellal; a three-blend of eugenol, α-terpineol and cinnamic alcohol; a four-blend of benzyl alcohol, phenethyl alcohol, phenethyl propionate and α-terpineol; and a five-blend of thymol, t-anethole, α-terpineol, eugenol and citronellal have been used as the pesticide. The pesticide affects the octopamine receptor site in the cockroach. The five-blend has been used as a pesticide for Asian armyworms and green peach aphid nymphs. Methods of use of the pesticides are disclosed.

5 Claims, 6 Drawing Sheets

OTHER PUBLICATIONS

W. Hertel et al, "The octopaminergic system of the invertebrates and its importance as insecticide target", Biol. Rundschau, vol. 27, No. 6, 1989, pp. 307–317.

Coats, J. R. et al, "Toxicity and Neurotoxic Effects of Monoterpenoids in Insects and Earthworms", ACS Symposium Series, 1991, pp. 305–316.

JP 01 016 706 A (Mikasa Kagaku Kigyo KK),"Non–Toxic Insecticide Composition", abstract, Jan. 20, 1989.

JP 05 039 203 A (Earth Seiyaku KK), "Safe Miticidal Compositions Having No Residual Toxicity", abstract, Feb. 19, 1993.

JP 04 091 003 A (Jumoku Chushutsusei), Acaracide Containing Alkyl–or Aralkyl Eugenol or Iso–eugenol, abstract, Mar. 24, 1992.

JP 52 110 823 A (Takasago Perfumery Co Ltd), "Insecticides Containing a 10C Ether", abstract, Sep. 17, 1977.

JP 02 049 703 A (Univ Kinki GH), "Insecticidal Composition for Killing Thrips Insects", abstract, Feb. 20, 1990.

JP 04 149 103 A (Taisho Pharm Co Ltd), "Acaricidal Composition to Control Indoor Dust Mites:", abstract, May 22, 1992.

Patent Abstract of Japan, JP 04 059703, Appl. No. 02166735 (T. Hasegawa Co., Ltd.), abstract Feb. 26, 1992.

Patent Abstracts of Japan, JP 59 222402 A, Appl. No. 58098489 (Otsuka Kagu Kogyo KK), abstract, Dec. 14, 1984.

Dev and Koul, "Insecticides of Natural Origin", Harwood Academic Publishers, Amsterdam 1997, pp. vii, viii, and 5 and 47–58.

Metcalf and McKelvey, Jr., editors, "The Future for Insecticides, Needs and Prospects", Wiley–Interscience, New York, 1976, pp. 97–113.

King, W. V., Chemicals Evaluated as Insecticides and Repellents at Orlando, Fla., Agricultural Handbook No. 69, U.S. Dept. of Agriculture, 1954, pp. 1–19, 26, 174 and 255.

* cited by examiner

PESTICIDAL ACTIVITY OF PLANT ESSENTIAL OILS AND THEIR CONSTITUENTS

CROSS REFERENCE TO RELATED APPLICATIONS

The present application is a continuation-in-part of patent application Ser. No. 09/302,198, filed Apr. 29, 1999 now abandoned.

BACKGROUND OF THE INVENTION

The present invention is directed to pesticidal activity and more particularly, to the effect on octopamine receptors in cockroaches and other invertebrates by plant essential oils and their constituents.

The present invention relates to a method of controlling pests and more particularly to a method of preparing and applying a pesticide which affects octopamine receptor sites in invertebrates.

Many chemicals and mixtures have been studied for pesticidal activity for many years with a goal of obtaining a product which is selective for invertebrates such as insects, arachnids and larvae thereof and has little or no toxicity to vertebrates such as mammals, fish, fowl and other species and does not otherwise persist in, and damage, the environment. Most products of which the applicants are aware and which have sufficient pesticidal activity to be of commercial significance, also have toxic or deleterious effects on mammals, fish, fowl or other species which are not the target of the product. For example, organophosphorus compounds and carbamates inhibit the activity of acetylcholinesterase in insects as well as in all classes of animals.

Several studies disclose the use of naturally occurring substances as insecticides but the references are mostly for a single species of insect or for a natural product which has many components. Thus, U.S. Pat. No. 5,118,506 to Eichofer discloses pine oil for use against fire ants. The pine oil is disclosed to be composed of thirty-eight (38) components and alpha-pinene is considered to be as effective as the unrefined pine oil. In U.S. Pat. No. 4,933,371, Hink et al control fleas and ticks with linalool, D-limonene and α-terpineol. Mixtures of these ingredients were not disclosed. Rod, in U.S. Pat. No. 5,653,991 discloses several monoterpenes which have insecticidal activity. Japanese Patent Abstract JP 05 039 203A discloses miticidal compositions having no residual toxicity. Patent Abstract of Japan JP 04 059 703, Application No. 02166735discloses a miticide. Coats et al in ACS Symposium Series 1991, pages 305–316 disclose insecticidal activity of several monoterpenoids. None of these references suggest a mode of action. Also, the references generally show that an active ingredient is useful against a narrow range of species of pests and do not have a broad spectrum of activity against many species of pests. These references do not disclose a preselected mixture of several active ingredients to provide an insecticide. The present applicants also have disclosed naturally occurring materials which have pesticidal activity in U.S. Pat. Nos. 6,004,569 and 6,183,767. Chlordimeform and related formamidines are known to act on octopamine receptors of insects but have been removed from the market because of cardiotoxic potential in vertebrates and carcinogenicity in animals and a varied effect on different insects. Also, very high doses are required to be toxic for certain insect species.

It is postulated that amidine compounds affect the octopamine sensitive adenylate cyclase present in insects [Nathanson et al, *Mol. Pharmacol* 20:68–75 (1981) and Nathanson, *Mol. Pharmacol* 28:254–268 (1985)]. Another study was conducted on octopamine uptake and metabolism in the insect nervous system [Wierenga et al, *J Neurochem* 54, 479–489 (1990)]. These studies were directed at nitrogen containing compounds which mimic the octopamine structure and do not include compounds consisting of only carbon, hydrogen and oxygen.

Insecticides such as trioxabicyclooctanes, dithianes, silatranes, lindane, toxaphen, cyclodienes and picrotoxin act on the GABA (gamma amino butyric acid) receptor. However, these products also affect mammals, birds, fish and other species.

There is a need for a broad spectrum pesticide which targets and controls only invertebrates and does not produce unwanted and harmful affects on other species, and a method for using this pesticide.

BRIEF SUMMARY OF THE INVENTION

It is an object of the invention to provide a method for using a pesticide which acts on the octopamine receptor site in the invertebrate, and particularly, the cockroach.

It is a further object to use naturally occurring substances as the pesticide.

In accordance with the teachings of the present invention, there is disclosed a method of killing cockroaches. Eugenol is prepared in a hydrocarbon solvent. The eugenol in the hydrocarbon solvent is applied to the cockroaches and the habitat thereof wherein the cockroaches are exposed to an effective dose to kill the cockroaches.

In further accordance with the teachings of the present invention, there is disclosed a method of killing cockroaches. A mixture is prepared of phenyl ethyl propionate, and eugenol and a carrier. The mixture is applied to the cockroaches and the habitat thereof, wherein the cockroaches are exposed to an effective dose to kill the cockroaches.

In still further accordance with the teachings of the present invention, there is disclosed a method of killing cockroaches. A mixture is prepared of carvacrol with a carrier. The mixture is applied to cockroaches and the habitat thereof, wherein the cockroaches are exposed to an effective dose to kill the cockroaches.

In addition, in accordance with the teachings of the present invention there is disclosed a method of killing cockroaches. A mixture is prepared of thyme oil with a carrier. The mixture is applied to cockroaches and the habitat thereof, wherein the cockroaches are exposed to an effective dose to kill the cockroaches.

Also, in accordance with the teachings of the present invention, there is disclosed a method of killing cockroaches. A mixture is prepared of thymol with a carrier. The mixture is applied to cockroaches and the habitat thereof, wherein the cockroaches are exposed to an effective dose to kill the cockroaches.

In another aspect there is disclosed a method of killing cockroaches. A mixture is prepared of an affector agent with a carrier. The affector agent is composed of carbon, hydrogen and oxygen atoms and is generally regarded as safe. The affector agent is an agonist or antagonist to octopamine receptor sites in the cockroaches and is selected from the group consisting of carvacrol, thyme oil, thymol and mixtures thereof. The mixture is applied to cockroaches and the habitat thereof, wherein the cockroaches are exposed to an effective dose to kill the cockroaches.

These and other objects of the present invention will become apparent from a reading of the following specification taken in conjunction with the enclosed drawings.

DESCRIPTION OF THE PREFERRED EMBODIMENTS

Most naturally occurring pesticides are used in their unpurified form which includes a host of other compounds as, for example, disclosed by Eichofer (U.S. Pat. No. 5,118,506). In these situations, it is difficult to ascertain what is the active ingredient and whether there is any synergistic effects from the multitude of other components or the specific ratios of one or more of these components within the natural product. The pure components of the mixtures have not been isolated and examined individually for activity and therefore provide no predictive value as to toxicity. Furthermore, the source of these naturally occurring pesticides is variable geographically and seasonally and providing a consistent active material or purity thereof is difficult. Thus, the prior art does not disclose a reproducible formulation. The prior art has not attempted to develop a blend of active components which complement each other and exhibit synergistic properties. The present invention addresses this aspect of pesticides as one of its objectives. The present invention also is directed to the naturally occurring plant substances such as essential oils and/or their constituents which are antagonists or agonists of octopamine receptor sites which are found in invertebrates. All of these naturally occurring pesticides have been used in food products and are generally regarded as safe (GRAS).

The present invention is directed primarily to a pesticide for the cockroach because this is a problematic insect which is found worldwide and is a most commonly used experimental insect to demonstrate effectiveness of an insecticide. Also the present invention is directed toward larvae because of their significance in agriculture and the need for a pesticide which is safe to disperse and has no toxic residue for food products.

A series of tests were conducted to demonstrate the activity of a group of purified naturally occurring plant essential oils and/or their constituents with the octopamine receptor sites of the ventral nerve cord of the American cockroach (*Periplaneta americana*).

Figure 1:
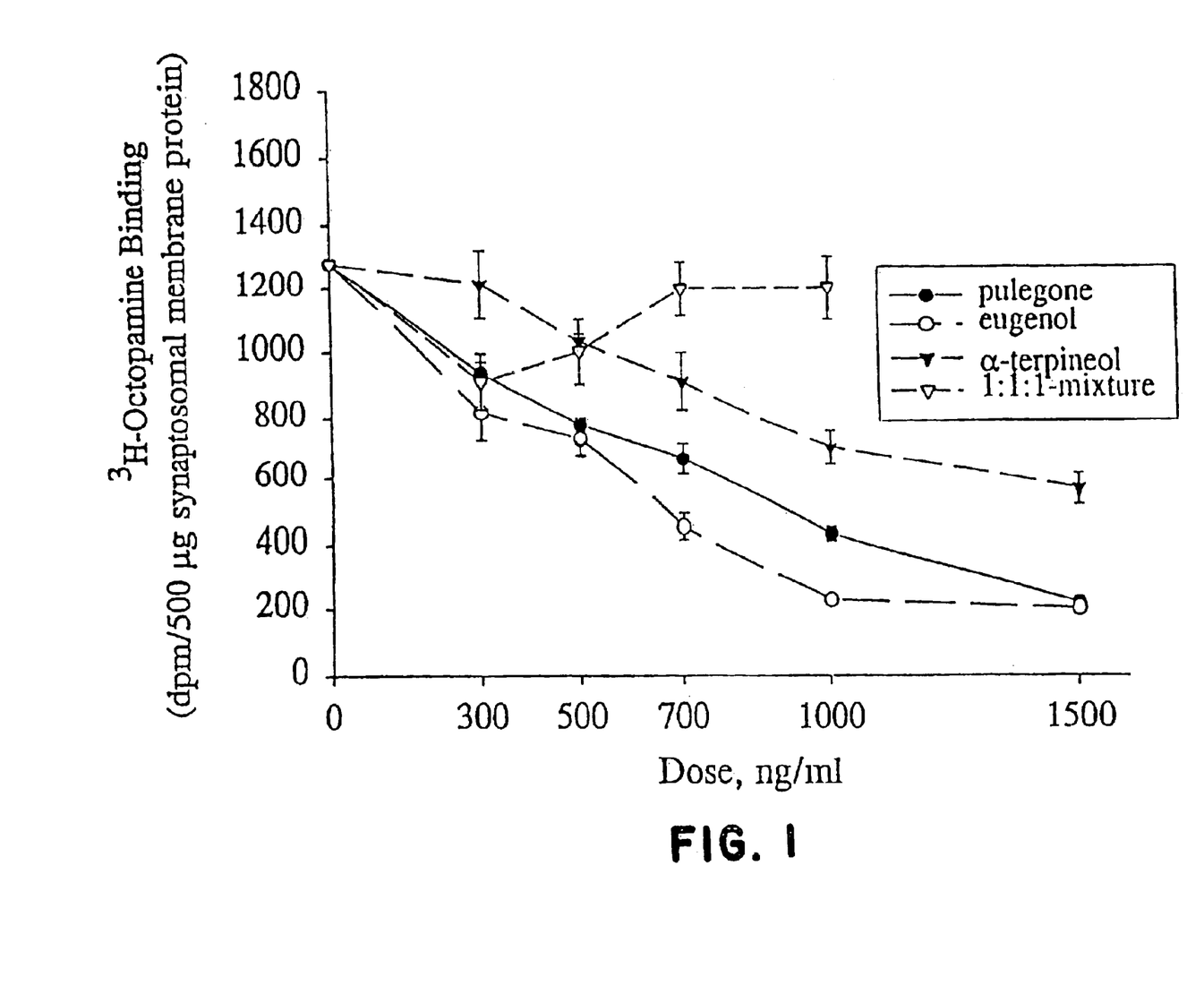
FIG. 1 is a graph of the dose of the insecticide vs. octopamine binding.

Different concentrations of unlabeled octopamine (OA) (20, 30, 40, 50, 60, 100 ng) were tested on the binding activity as a positive control. Test chemicals were dissolved in acetone before the assay. Different concentrations of the test chemicals were added directly to the protein preparation from ventral nerve cord. The same amount of solvent (1 μl 0.1%) were added to the control samples. All assays with test chemicals were run in the presence and absence of 50 ng OA. All chemicals were added to the protein extract 20 min prior the addition of radio labeled $^3$H-OA(100,000 cpm/sample). After 30 min at 24° C. of the addition of $^3$H-OA, the reaction was stopped by the addition of ice-cold Tris buffer, and the samples were filtered through GF/C membrane using water vacuum. After two washes each with 5 ml Tris buffer, the membrane was removed, air dried and the radioactivity was counted in 4 ml liquid scintillation solution. The specific binding was calculated as the difference between the values in the presence and absence of unlabeled OA. All data are calculated as the mean±standard deviation of 5 assays. The data is shown in Table 1 and FIG. 1.

TABLE 1

In vitro effect of different concentrations of test chemicals on $^3$H-OA binding activity.

| | cpm $^3$H-OA/500 μg protein | | | | |
|---|---|---|---|---|---|
| | 300 ng | 500 ng | 700 ng | 1000 ng | 1500 ng |
| Control (solvent) | 1280 ± 259 | — | — | — | — |
| pulegone | 936 ± 33 | 778 ± 22 | 662 ± 51 | 435 ± 22 | 217 ± 18 |
| eugenol | 818 ± 93 | 730 ± 59 | 453 ± 39 | 226 ± 15 | 200 ± 17 |
| α-terpineol | 1213 ± 110 | 1031 ± 24 | 910 ± 88 | 700 ± 88 | 565 ± 47 |
| Mixture[a] 1:1:1 | 910 ± 85 | 1001 ± 99 | 1196 ± 86 | 1200 ± 86 | ND |

[a]Mixture of all three chemicals was tested as ⅓concentration of each individual test concentration.

It would be expected that the mixture of the three (3) compounds would be more tightly bound than any of the individual compounds. However, with increased dose, the mixture was bound less strongly than any of the individual components. This demonstrates that simple mixing of naturally occurring plant essential oils and/or their constituents is not synergistic but a selective blending is required for mixtures in order to increase the effectiveness of any mix.

Additional tests were conducted on radio labeled octopamine using other purified naturally occurring materials as given in Tables 2 and 3.

TABLE 2

In vitro effect of test chemicals on $^3$H-OA binding
of synaptosomal membrane protein from American cockroach
dpm $^3$H-OA/500 µg protein

|  | 1000 ng/ml | 500 ng/ml |
|---|---|---|
| Control (solvent) | 930 ± 89 | 1101 ± 120 |
| Citronellol | 557 ± 43 | 999 ± 65 |
| d-limonene | 866 ± 71 | 1194 ± 101 |
| Eucaluptol | 653 ± 36 | 865 ± 45 (antagonist) |
| Carvacol | 2366 ± 149 (agonist) | ND |
| Citronellal 80 | 526 ± 33 | 725 ± 95 (antagonist) |

All of the test chemicals are plant essential oils, d-limonene has no oxygenated functional group and evidences no activity against octopamine receptor sites.

TABLE 3

In vitro effect of 500 and 1000 ng/ml of test chemicals on $^3$H-OA
binding of synaptosomal membrane protein from American cockroach
cpm $^3$H-OA/500 µg protein

|  | 1000 ng/ml | 500 ng/ml |
|---|---|---|
| Control (solvent) | 1915 ± 110 | 1385 ± 101 |
| Thyme OiL | 993 ± 77 | 1387 ± 121 |
| Thymol | 806 ± 71 | 1310 ± 91 |
| Thyme Red | 1101 ± 93 | 1290 ± 74 |
| Thyme White | 955 ± 56 | 1307 ± 35 |
| Trans-Anethole | 970 ± 87 | 1104 ± 110 (antagonist) |
| Vanillin | 700 ± 55 | 1030 ± 83 (antagonist) |
| α-phellandrene | ND | 2353 ± 343 (agonist) |
| Eucalyptol | ND | 1637 ± 095 |
| Piperonyl alcohol | 862 ± 61 | 1124 ± 083 (antagonist) |
| Piperonyl acetate | 519 ± 52 | 1090 ± 092 (antagonist) |
| Piperonal | ND | 1680 ± 131 |
| R-limonene | ND | 1436 ± 133 |
| Ethyl vanillin | ND | 1723 ± 119 |
| Phenethyl propionate | ND | 0173 ± 022 (antagonist) |
| Methyl salicylate | ND | 0084 ± 009 (antagonist) |
| p-cymene | 804 ± 057 | 1142 ± 074 (antagonist) |
| Iso-eugenol | 499 ± 029 | 1091 ± 080 (antagonist) |
| Guaiacol | ND | 1787 ± 151 |

These data show that methyl salicylate and phenethyl propionate are antagonists which are most strongly bound to the octopamine.

Based on this data the chemicals may be classified with respect to octopamine receptor sites (OAR) as:

Class I: OAR Antagonists:
  a. extremely high OAR antagonists: phenethyl propionate and methyl salicylate;
  b. high OAR antagonists: pulegone and eugenol;
  c. moderate OAR antagonists: iso-eugenol, α-terpineol citronellal 80, p-cymene and trans-anethole.
Class II: OAR Agonists:
  carvacrol and α-phellandrene.
Class III: Non-OAR Specific Toxicants:
  eucalyptol, piperonal, R-limonene and d-limonene;
  ethyl vanillin, guaiacol, thyme oil, thyme red and thyme;
  white thyme oil and thymol.

Figure 2:
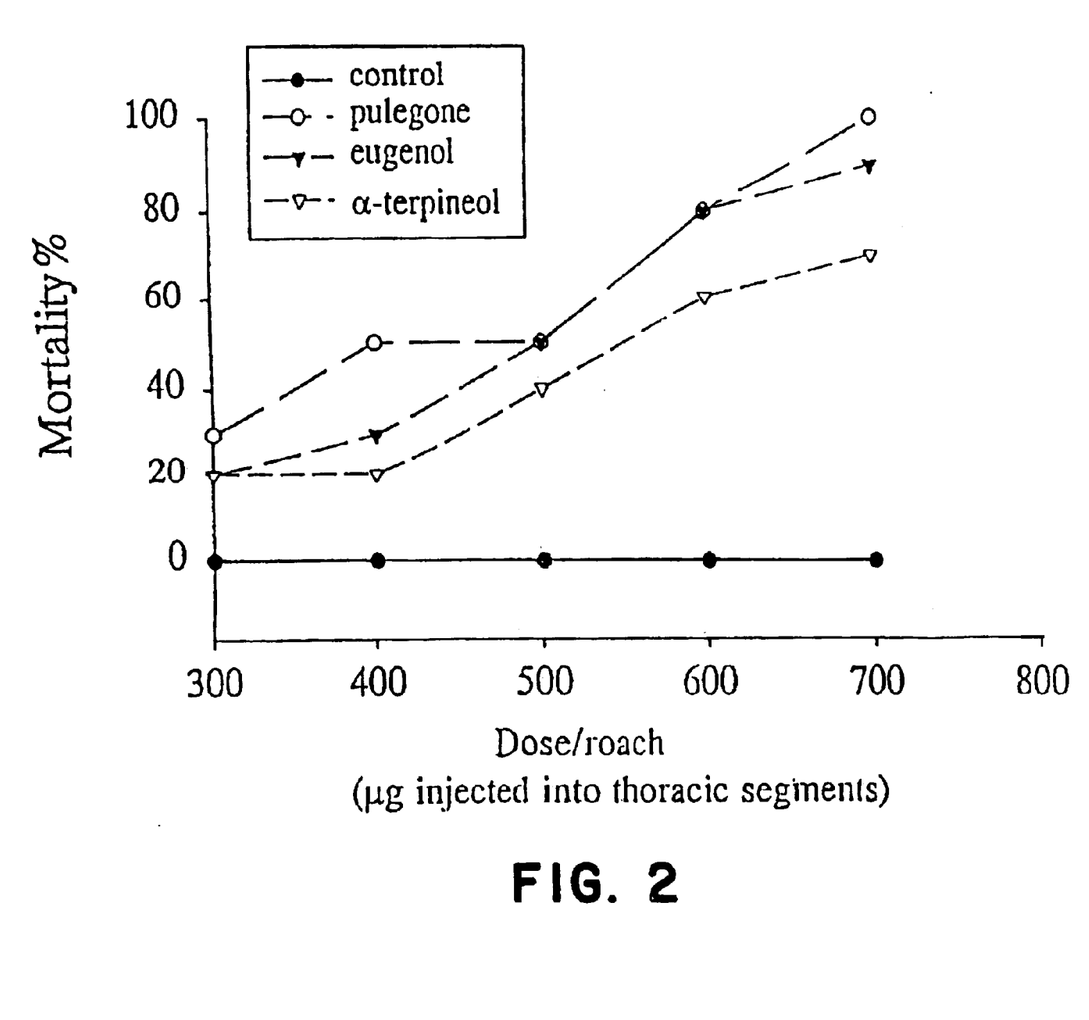
FIG. 2 is a graph of mortality of plant essential oils vs. dose.

Further studies were conducted to determine the LD 50 of purified naturally occurring plant essential oils and/or their constituents. Test chemicals (500 µg/roach) were dissolved in acetone prior to the injection into the thoracic and abdominal segments of the American cockroach. Ten roaches per dose were used. Another group of ten roaches received the same volume of vehicle only (0.5 µl) and used as a control group. Mortality was recorded 24, 48, and 72 hours after exposure. The results are given in Tables 4 and 5 and FIG. 2.

TABLE 4

Time-course lethal effect of test chemicals on American roaches
Mortality

|  | 24 hr. | 48 hr. | 72 hr. |
|---|---|---|---|
| control | 0/10 | 0/10 | 1/10 |
| pulegone | 6/10 | 6/10 | 7/10 |
| eugenol | 6/10 | 6/10 | 6/10 |
| α-terpineol | 4/10 | 4/10 | 5/10 |
| phenethyl alcohol | 0/10 | 0/10 | 0/10 |
| citronellal | 0/10 | 0/10 | 0/10 |
| d-limonene | 0/10 | 0/10 | 0/10 |
| eucaluptol | 0/10 | 0/10 | 0/10 |
| oil of thyme | 0/10 | 0/10 | 0/10 |

No lethal effect was observed when the test chemicals were injected through the end of the abdominal segment, except pulegone (50 µg) which induced 20% mortality 48 hr. after treatment.

TABLE 5

Dose response effect on mortality of American cockroaches

Mortality 24 hr after treatment

|  | 300 µg | 400 µg | 500 µg | 600 µg | 700 µg |
|---|---|---|---|---|---|
| control | 0/10 | 0/10 | 0/10 | 0/10 | 0/10 |
| pulegone | 3/10 | 5/10 | 5/10 | 8/10 | 10/10 |
| eugenol | 2/10 | 3/10 | 5/10 | 8/10 | 9/10 |
| α-terpineol | 2/10 | 2/10 | 4/10 | 6/10 | 7/10 |

To further establish the effect of the purified naturally occurring plant essential oils and/or their constituents on the American cockroach, a 300 µg amount of the chemical was applied to the thoracic segment of an intact and alive American cockroach. The heart beats/30 seconds was measured. The heart of the cockroach is known to have a high concentration of octopamine receptors and the heart beat is considered an important measurement to indicate the effect of the applied chemicals to the octopamine receptors. The results of this study are given in Table 6.

TABLE 6

Structure-activity relationship effect of test chemicals
on the heartbeat of American cockroaches

| | Heart beat/30 sec | |
|---|---|---|
| Test Chemicals | before treatment | 30 min after treatment |
| α-Terpineol | 58 ± 4 | 32 ± 2* |
| Eugenol | 55 ± 3 | 24 ± 1* |

TABLE 6-continued

Structure-activity relationship effect of test chemicals on the heartbeat of American cockroaches

| Test Chemicals | Heart beat/30 sec | |
|---|---|---|
| | before treatment | 30 min after treatment |
| Cinnamic Alcohol | 52 ± 2 | 54 ± 3 |
| Phenethyl Alcohol | 47 ± 2 | 29 ± 2* |
| Benzyl Acetate | 45 ± 2 | 42 ± 1 |
| Benzyl Alcohol | 45 ± 3 | 39 ± 2 |
| 3-blend (a) | 52 ± 1 | 67 ± 5* |
| 5-blend (b) | 55 ± 2 | 27 ± 1* |
| α-Terpineol + Eugenol | 56 ± 1 | 19 ± 2* |
| α-Terpineol + Phenethyl Alcohol | 57 ± 2 | 45 ± 1* |
| Eugenol + Phenethyl Alcohol | 65 ± 4 | 28 ± 1* |

Data are the mean (±SD) of three roaches. *Significant difference, $P < 0.05$, Student t-test.
(a) The 3-blend material is a 1:1:1 mixture, by weight, of eugenol, α-terpineol and cinnamic alcohol.
(b) The 5-blend material is a mixture, by weight, of 40% thymol, 25% t-anethole, 15% α-terpineol, 10% eugenol and 10% citronellal.

It is believed that the 3-blend acts synergistically on the heart of the cockroach to increase the heart beat to kill the insect. This is evidenced by the hyperactivity of the exposed cockroaches. Based on the decreased heart beat produced by α-terpineol and eugenol and the relatively unchanged heart beat after exposure to cinnamic alcohol, the increased heart beat of the 3-blend is unexpected.

A "3-blend" mixture of eugenol, α-terpineol and cinnamic alcohol in a 1:1:1 ratio, by weight, was prepared in acetone.

Figure 3:
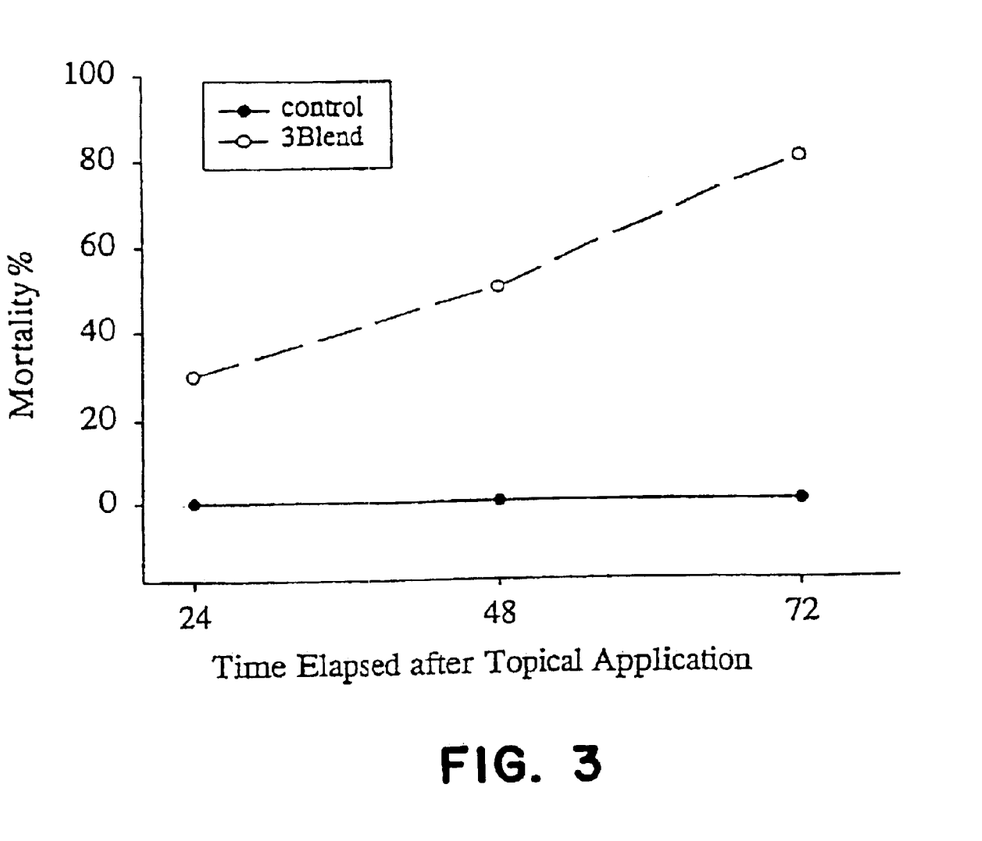
FIG. 3 is a graph of mortality of three blend vs. time after topical application.

In order to show the toxicity of the "3-blend" to cockroaches, 0.5 μl of the acetone solution containing 1 mg of "3-blend" was applied topically to the cockroach and mortality determined after 24, 48 and 72 hours. A control was conducted which was acetone without any "3-blend". FIG. 3 shows that approximately 30% of the cockroaches had died within 24 hours of exposure and approximately 80% of the cockroaches had died within 72 hours.

Additional studies were conducted to demonstrate the efficacy of the purified naturally occurring materials and various blends of the materials. In the test, a known amount of the test material was dissolved in a known volume of acetone and applied to small jars and all inner bottom surfaces were covered. The bottom surface of each jar is approximately 250 cm². One hour after the acetone had completely evaporated, five American cockroaches were introduced to each jar. Control jars were treated exactly as above but with the known amount of acetone only.

Test results with the "3-blend" mixture is given in Table 7.

TABLE 7

Time-course effect of 3-blend (1 mg/jar) on American cockroaches exposed to pre-treated surface one hour after 3-blend application.*

| Time (min) | Mortality |
|---|---|
| 10 | 3/5 |
| 15 | 3/5 |
| 20 | 4/5 |
| 30 | 5/5 |

*No death in insects exposed to surface treated with acetone alone.

A "4-blend" mixture was prepared which, by weight, is benzyl alcohol 25%, phenethyl alcohol 25%, phenethyl propionate 25%, and α-terpineol 25%. The results of the "cross walk" jar tests are in Table 8 in which the "4-blend" was dispersed as an aerosol and a dust in the jar.

TABLE 8

Toxicity of 4-blend and 3-blend against American cockroach as determined by "cross walk".

| | % Mortality | |
|---|---|---|
| Chemical Code | 10 mg/jar | 50 mg/jar |
| Benzyl alcohol | 100 | — |
| 4-blend (aerosol) | 100 | — |
| Control (aerosol) | 40 | 40 |
| Benzyl alcohol, sesame oil and emulsifier | 100 | — |
| 4-blend (dust) | 100 | — |
| Benzyl alcohol (dust) | 70 | 100 |
| Control (dust) | 0 | 0 |
| 3-blend in acetone | 100 | — |
| 4-blend in acetone | 80 | 100 |

Table 8 shows the tests conducted with aerosol and dust. These are only two of the carriers in which the pesticides were mixed.

The term "carrier" as used herein means a material, which may be inorganic or organic and of synthetic or natural origin, with which the active compound is mixed or formulated to facilitate its application to the plant, seed, soil or other object to be treated, or its storage, transport and/or handling. In general, any materials that may be customarily employed as a carrier in pesticidal, herbicidal, or fungicidal formulations, are suitable for use with the present invention. The inventive pesticidal compositions of the present invention may be employed alone or in the form of mixtures with such solid and/or liquid dispersable carrier vehicles and/or other known compatible active agents, especially plant protection agents, such as other pesticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The pesticidal compositions of the present invention can be formulated or mixed with, if desired, conventional inert (i.e. plant compatible or herbicidally inert) pesticide diluents or extenders of the type usable in conventional pesticide formulations or compositions, e.g. conventional pesticide dispersable carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, coating compositions for use on seeds, and formulations used with burning equipment, such as fumigating cartridges, fumigating cans and fumigating coils, as well as ULV cold mist and warm mist formulations, etc.

Formulations containing the pesticidal compositions of the present invention may be prepared in any known manner, for instance by extending the pesticidal compositions with conventional pesticide dispersable liquid diluent carriers and/or dispersable solid carriers optionally with the use of carrier vehicle assistants, e.g. conventional pesticide surface-active agents, including emulsifying agents and/or 
dispersing agents, whereby, for example, in the case where water is used as diluent, organic solvents may be added as auxiliary solvents. Suitable liquid diluents or carriers include water, petroleum distillates, or other liquid carriers with or without surface active agents. The choice of dispersing and emulsifying agents and the amount employed is dictated by the nature of the composition and the ability of the agent to facilitate the dispersion of the pesticidal compositions of the present invention. Generally, it is desirable to use as little of the agent as is possible, consistent with the desired dispersion of the pesticidal compositions of the present invention in the spray so that rain does not re-emulsify the pesticidal compositions of the present invention after it is applied to the plant and wash it off the plant. Non-ionic, anionic, amphoteric, or cationic dispersing and emulsifying agents may be employed, for example, the condensation products of alkaline oxides with phenol and organic acids, alkyl aryl sulfonates, complex ether alcohols, quaternary ammonium compounds, and the like.

Liquid concentrates may be prepared by dissolving a composition of the present invention with a non-phytotoxic solvent and dispersing the pesticidal compositions of the present inventions in water with the acid of suitable surface active emulsifying and dispersing agents. Examples of conventional carrier vehicles for this purpose include, but are not limited to, aerosol propellants which are gaseous at normal temperatures and pressures, such as Freon; inert dispersable liquid diluent carriers, including inert organic solvents, such as aromatic hydrocarbons, e.g. benzene, toluene, xylene, alkyl naphthalenes, etc., halogenated especially chlorinated, aromatic hydrocarbons, e.g. chlorobenzenes, etc., cycloalkanes, e.g. cyclohexane, etc., paraffins, e.g. petroleum or mineral oil fractions, isoparaffinic hydrocarbons (such as "Isopar M" sold by Exxon Corp.) chlorinated aliphatic hydrocarbons, e.g. methylene chloride, chloroethylenes, etc., alcohols, e.g. methanol, ethanol, propanol, butanol, glycol, etc., as well as ethers and esters thereof, e.g. glycol monomethyl ether, etc., amines, e.g. ethanolamine, etc., amides, e.g. dimethyl formamide etc., sulfoxides, e.g. dimethyl sulfoxide, etc., acetonitrile, ketones, e.g. acetone, methyl ethyl ketone, methyl isobutyl ketone, cyclohexanone, etc., and/or water; as well as inert dispersable finely divided solid carriers such as ground natural minerals, e.g. kaolins, clays, vermiculite, alumina, silica, chalk, i.e. calcium carbonate, talc, attapulgite, montmorillonite, kieselguhr, etc., and ground synthetic minerals, e.g. highly dispersed silicic acid, silicates, e.g. alkali silicates, etc.

Surface-active agents, i.e., conventional carrier vehicle assistants, that may be employed with the present invention include, without limitation, emulsifying agents, such as non-ionic and/or anionic emulsifying agents, e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc., and/or dispersing agents such as lignin, sulfite waste liquors, methyl cellulose, etc.

In the preparation of wettable powders, dust or granulated formulations, the active ingredient is dispersed in and on an appropriately divided carrier. In the formulation of the wettable powders the aforementioned dispersing agents as well as lignosulfonates can be included. Dusts are admixtures of the compositions with finely divided solids such as talc, attapulgite clay, kieselguhr, pyrophyllite, chalk, diatomaceous earths, vermiculite, calcium phosphates, calcium and magnesium carbonates, sulfur, flours, and other organic and inorganic solids which act as carriers for the pesticide. These finely divided solids preferably have an average particle size of less than about 50 microns. A typical dust formulation useful for controlling insects contains 1 part of pesticidal composition and 99 parts of diatomaceous earth or vermiculite. Granules may comprise porous or nonporous particles. The granule particles are relatively large, a diameter of about 400–2500 microns typically. The particles are either impregnated or coated with the inventive pesticidal compositions from solution. Granules generally contain 0.05–15%, preferably 0.5–5%, active ingredient as the pesticidally-effective amount. Thus, there is contemplated formulations with solid carriers or diluents such as bentonite, fullers earth, ground natural minerals, such as kaolins, clays, talc, chalk, quartz, attapulgite, montmorillonite or diatomaceous earth, vermiculite, and ground synthetic minerals, such as highly-dispersed silicic acid, alumina and silicates, crushed and fractionated natural rocks such as calcite, marble, pumice, sepiolite and dolomite, as well as synthetic granules of inorganic and organic meals, and granules of organic materials such as sawdust, coconut shells, corn cobs and tobacco stalks. Adhesives, such as carboxymethyl cellulose, natural and synthetic polymers, (such as gum arabic, polyvinyl alcohol and polyvinyl acetate), and the like, may also be used in the formulations in the form of powders, granules or emulsifiable concentrations.

If desired, colorants such as inorganic pigments, for example, iron oxide, titanium oxide and Prussian Blue, and organic dyestuffs, such as alizarin dyestuffs, azo dyestuffs or metal phthalocyanine dyestuffs, and trace elements, such as salts of iron, manganese, boron, copper, cobalt, molybdenum and zinc may be used.

If desired, volatile organic compounds suitable as the fragrance ingredient for use in formulations for household or pet applications, include, but are not limited to, amyl salicylate, citronellal, citronelloxyacetaldehyde, cyclamen aldehyde, citronellyl isobutyrate, coumarin, cyclohexyl acetate, cyclohexyl butyrate, diethyl malonate, ethyl 2-acetyl-5-ketohexanoate, isobornyl acetate, linalool, phenethyl alcohol, undecanol, alpha-hexylcinnamaldehyde, 2-methylhexanol, hexalon, phenylacetaldehyde, cis-3-hexen-1-ol, cyclamal, veronol, eugenol, Lyral, Galaxolide, Citralva, musk ambrette, terpinyl acetate, geraniol, alpha-damascone, alpha-methylionone, and the like. Illustrative of volatile essential oils are oil of Bergamot, cedar leaf, cedar wood, geranium, lavender, white cedar, sandalwood oil, rose extract, violet extract, galbanum oil, and the like. Synthetic types of organic fragrances are described in publications such as U.S. Pat. Nos. 4,314,915; 4,411,829; and 4,434,306.

In commercial or agricultural applications, the present invention encompasses carrier composition mixtures in which the pesticidal compositions are present in an amount substantially between about 0.01–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all formulations that comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The pesticidal compositions can also be used in accordance with so-called ultra-low-volume process, i.e. by applying such compounds or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed. In this process it is possible to use highly concentrated liquid compositions with said liquid carrier vehicles containing from about 20 to 95% by weight of the pesticidal compositions or even the 100% active substances alone, e.g. about 20–100% by weight of the pesticidal compositions. The mixture of active materials may be applied, without limitation, in sufficient amounts so as to provide about 0.2 to 2 and preferably about 0.5 to 1.5 pounds of active materials per acre. Moreover, the required amount of the pesticidal composition contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95% by weight and in the solid formulations from about 05. to 90% by weight. Satisfactory sprays, dusts, or granules for general use contain from about ¼ to 15 pounds of active synergistic and residual compositions per acre.

In another experiment, roaches were exposed to treated jars with 1 ml (approximately equivalent to 1000 mg toxicant) of the selected product for 5 seconds, then, transferred into untreated jars. Mortality was recorded 60 minutes later. The jar has a bottom with a surface area of approximately 250 $cm^2$.

TABLE 9

Toxicity of "4-blend" to American cockroach as determined by "cross walk".

| Chemical Code | % Mortality |
| --- | --- |
| Control (aerosol) | 0 |
| Benzyl alcohol, sesame oil, emulsifier | 100 |
| Control (water) | 0 |
| 4-blend (dust) | 100 |
| Benzyl alcohol (dust) | 100 |
| Control (dust) | 0 |
| 3-blend in acetone | 100 |
| 4-blend in acetone | 100 |

Note that the higher concentration (1000 mg) of pesticide was able to produce 100% mortality in the extremely brief exposure of only five seconds.

Figure 4:
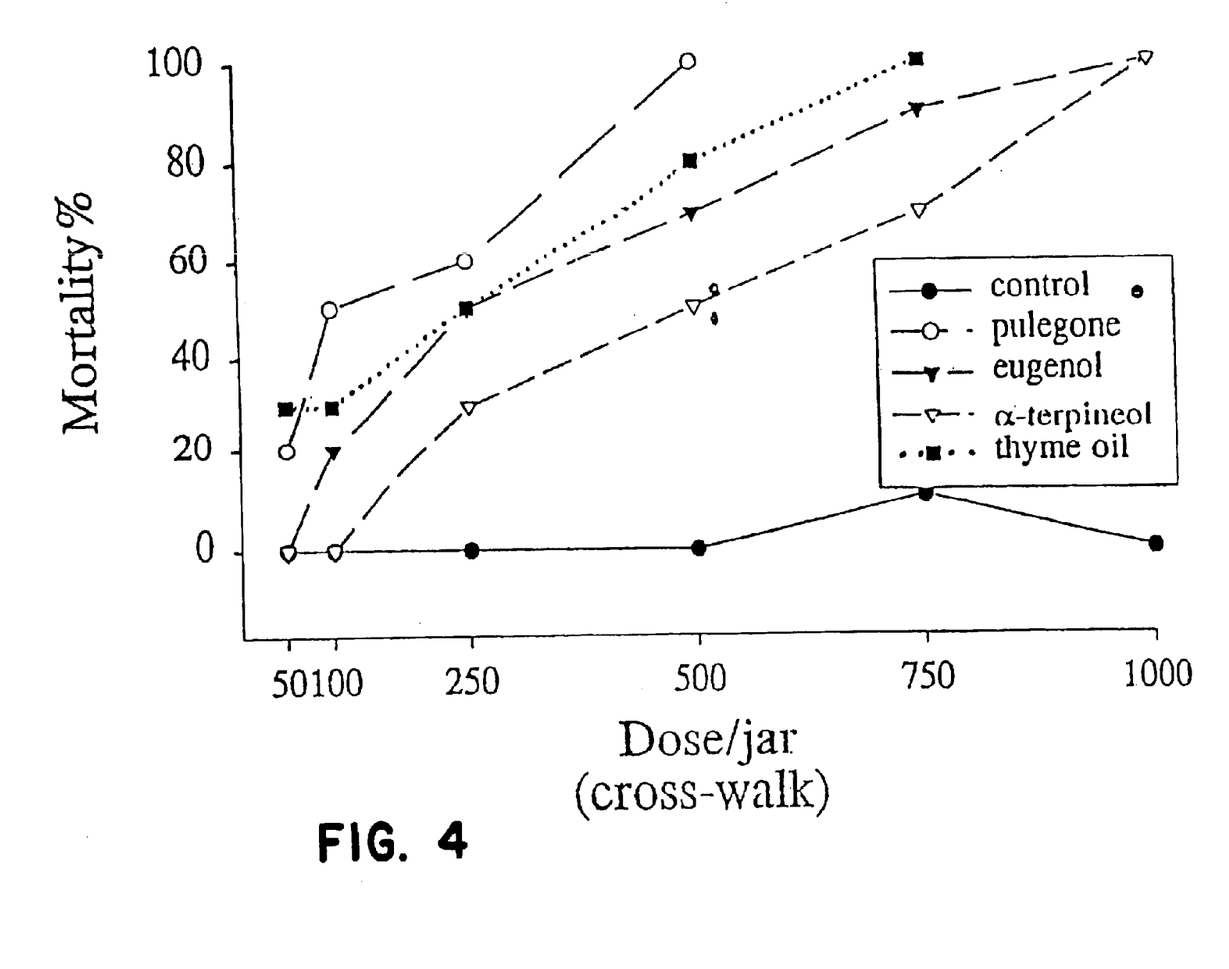
FIG. 4 is a graph of mortality of plant essential oils vs. dose.

Additional "cross walk" data for several purified naturally occurring plant materials are given in FIG. 4. In this test, the acetone solution of the test material was placed in the jar and the roach inserted into the jar after the acetone had evaporated.

Table 10 provides "cross walk" data for additional purified naturally occurring materials. Mortality was measured 24 hours after exposure.

TABLE 10

Toxicity of purified naturally occurring compounds to cockroaches in "cross walk".

| | % Mortality Test Concentrations (mg/jar) | | | | | |
| --- | --- | --- | --- | --- | --- | --- |
| Test Chemicals | 10 | 20 | 30 | 40 | 50 | 100 |
| Phenethyl propionate | 30 | 40 | 60 | 90 | 100 | 100 |
| Pulegone | 100 | — | — | — | — | — |
| Methyl salicylate | 0 | 20 | 40 | 80 | 100 | — |
| Oil of thyme | 0 | 10 | 80 | 100 | — | — |
| Carvacrol | 0 | 20 | — | 50 | 80 | 100 |
| Thymol | — | — | — | 80 | — | 100 |

The "4-blend" and the individual constituents of the "4-blend" were tested using 10 cockroaches for each "cross walk" treatment. In addition, pyrethrins were tested separately and mixed with the various components. The data is given in Table 11.

TABLE 11

Synergistic effect of naturally occurring plant materials on American cockroach. Ten cockroaches were used for each cross-walk treatment.

| | % Mortality | | |
| --- | --- | --- | --- |
| Treatment | 24 hr. | 48 hr. | 72 hr. |
| Control | 0 | 0 | 0 |
| 1-phenethyl alcohol | 0 | 0 | 0 |
| 2-α-terpineol | 20 | 30 | 60 |
| 3-benzyl alcohol | 0 | 20 | 40 |
| 4-phenethyl propionate | 100 | — | — |
| 5-eugenol | 100 | — | — |
| 6-pyrethrins (2 mg/jar) | 0 | 0 | 10 |
| 1 + 2 + 3 | 40 | 70 | 80 |
| 1 + 2 + 3 + 4 | 60 | 100 | — |
| 1 + 2 + 3 + 4 + 5 | 100 | — | — |
| 1 + pyrethrins | 0 | 20 | 20 |
| 2 + pyrethrins | 40 | 60 | 100 |
| 3 + pyrethrins | 20 | 40 | 80 |
| 4 + pyrethrins | 100 | — | — |
| 5 + pyrethrins | 100 | — | — |

A concentration of 100 mg/jar was used for each individual alone. In the co-treatment experiment without pyrethrins, 20 mg/jar for each chemical was used. In the cotreatment experiment with pyrethrins, 20 mg/jar for the naturally occurring plant material was used. Pyrethrins was used at 2 mg/jar. Thus, the concentration of each component was significantly reduced as compared to the concentrations of the non-blended materials. It was noted above that the mortality is dependent upon concentration. Eugenol demonstrated synergistic effects with the 4-blend as shown in that 1+2+3+4 gave 60% mortality at 24 hours and 100% at 48 hour. and 1+2+3+4+eugenol produced 100% mortality at 24 hours. Some synergism is found between pyrethrins and either α-terpineol or benzyl alcohol.

The above data demonstrate that purified naturally occurring plant essential oils and/or their constituents have pesticidal activity against cockroaches. Phenethyl propionate, methyl salicylate pulegone, carvacrol have high pesticidal activity which is attributed to these compounds being highly antagonistic or agonistic to octopamine receptor sites in insects. The pesticidal activity of thyme and thyme oil is believed to be due to an interaction with calcium communication in the pests. Also various bends of purified naturally occurring plant essential oils and/or their constitutents have increased pesticidal activity based on synergistic action between the components of the respective blends. Synergistic action is not produced by every combination of plant essential oils and the blends of the present invention have been found to have this type of activity. Also, the blends of the present invention are believed to be effective by acting on the octopamine receptor sites in the cockroaches or by producing pesticidal activity through dual pathways of neural activity, such as in the case of thymol and thyme oil.

Additional synergistic testing was conducted on $3^{rd}$ instar Asian armyworms (Spodoptera litura). The results are given in Table 12 which were conducted with the samples diluted 1:400 with water. The number of replicates is given as "n".

TABLE 12

Pesticidal activity on Asian armyworms.

| Treatment | Mortality (%) (n = 100) | Treatment | Mortality (%) (n = 50) |
| --- | --- | --- | --- |
| 5-blend | 73 | Thymol | 98 |
| Phenethyl propionate (PEP) | 8 | PEP | 2 |
| 5B + PEP (1:1) | 84 | Thymol + PEP (1:1) | 84 |
| Control | 1 | Control | 0 |

Phenethyl propionate (PEP) has relatively low activity but can be used as a diluent for 5-blend or thymol, without appreciable loss of bioactivity. Note that at the 1:1 dilution, the concentrations of the respective components are ½ of the undiluted material which is a factor in the mortality data. PEP is synergistic to thymol and 5-blend. Additional experiments were conducted at lower concentrations as shown in Table 13.

TABLE 13

Pesticidal activity on Asian armyworms

| Treatment | Mortality (%) (n = 50) | Treatment | Mortality (%) (n = 50) |
| --- | --- | --- | --- |
| 5-blend, 1:500 | 74 | Thymol, 1:500 | 29 |
| 5B + PEP (1:1), 1:500 | 76 | PEP | 2 |
| 5-blend, 1:600 | 60 | Th + PEP, 1:1 | 30 |
| PEP, 1:600 | 24 | Control | 0 |
| 5B + PEP (1:1), 1:600 | 74 | | |
| Control | 0 | | |

These data corroborate the previous results completely with respect to 5-blend, thymol, PEP and the mix of these. Owing to the potential significance of these findings, a further set of experiments were conducted at a dilution rate of 1:500 and n=150 as in Table 14. Lower concentrations of active ingredients reduce the cost per treatment, as well as the risk of exposure to the environment and phytotoxicity to plants and crops.

TABLE 14

Pesticidal activity on Asian armyworms.

| Treatment | Mortality (%) (n = 150) | Treatment | Mortality (%) (n = 150) |
| --- | --- | --- | --- |
| 5-blend | 66.7 | Thymol | 24.5 |
| PEP | 27.3 | PEP | 4 |
| 5B + PEP (1:1) | 71.3 | Th + PEP, 1:1 | 21 |
| Control | 1.3 | Control | 0 |

The data of Tables 12–14 confirm the pesticidal activity of 5-blend and PEP over a range of dilutions. Thymol is more active at the lower dilution (1:400) and activity decreases as dilution increases. The action is still synergized with PEP.

The LD 50 of oil of thyme to Asian armyworms was determined by the topical application of acetone solutions to the dorsal region of the caterpillar. In each glass dish there were 10 larvae. The data in Table 15 show an LD 50=43.7 $\mu g/\mu l$/larvae with 95% confidence=40.8–46.7.

TABLE 15

Mortality for oil of thyme to Asian armyworms

| | dish | | | | |
| --- | --- | --- | --- | --- | --- |
| Dose ($\mu$g/larvae) | 1 | 2 | 3 | 4 | total # dead out of 40 |
| 0 | 0 | 0 | 0 | 0 | 0 |
| 24 | 0 | 0 | 0 | 0 | 0 |
| 34 | 1 | 2 | 2 | 4 | 9 (22%) |
| 46 | 5 | 5 | 6 | 5 | 21 (52.5%) |
| 60 | 10 | 8 | 9 | 8 | 35 (87.5%) |
| 75 | 10 | 10 | 10 | 10 | 40 (100%) |

Thus, oil of thyme is also shown to have toxicity to both the American cockroach and the Asian armyworm.

Figure 5:
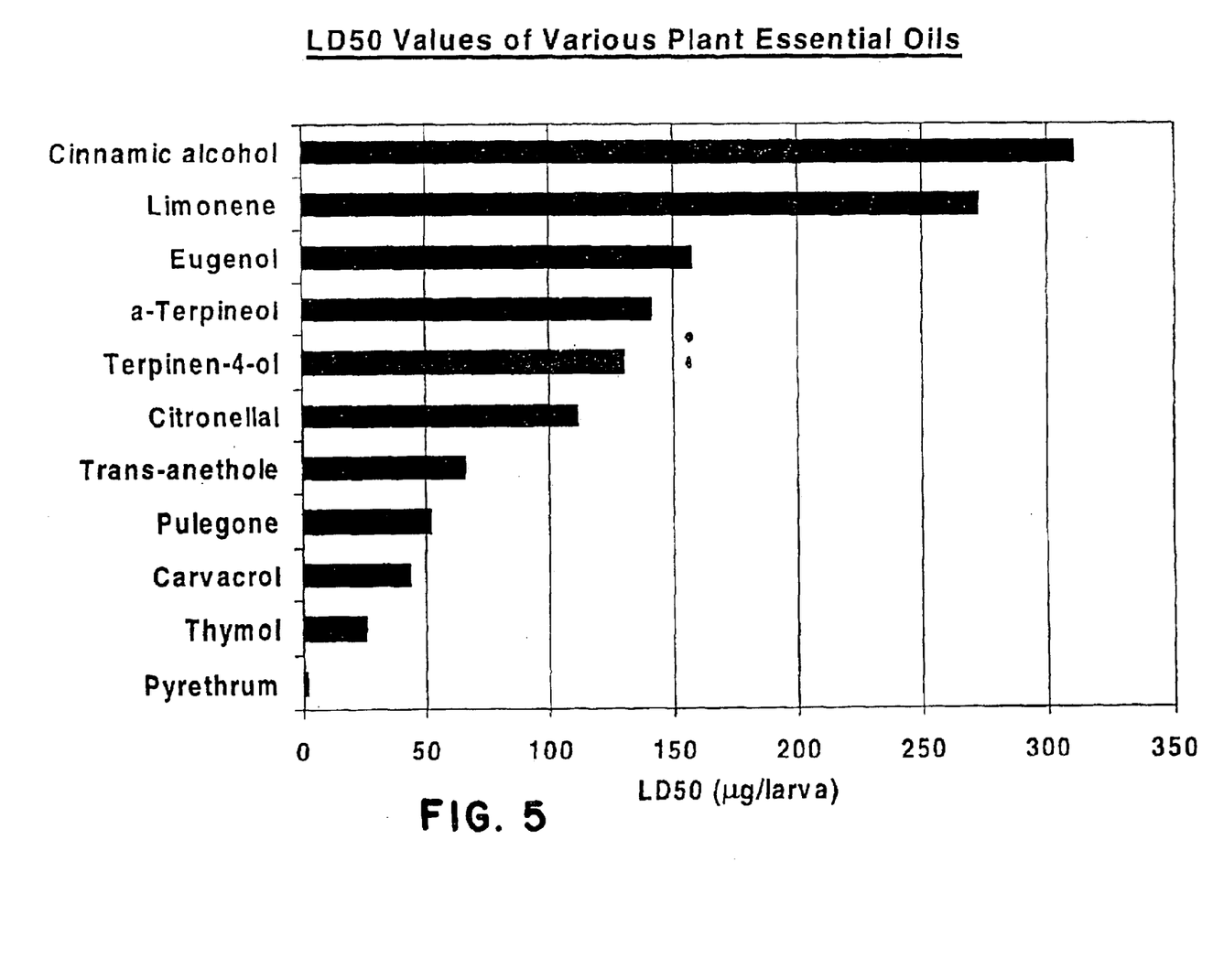
FIG. 5 is a graph of the LD 50 values of various plant essential oils vs. larvae.
Figure 6:
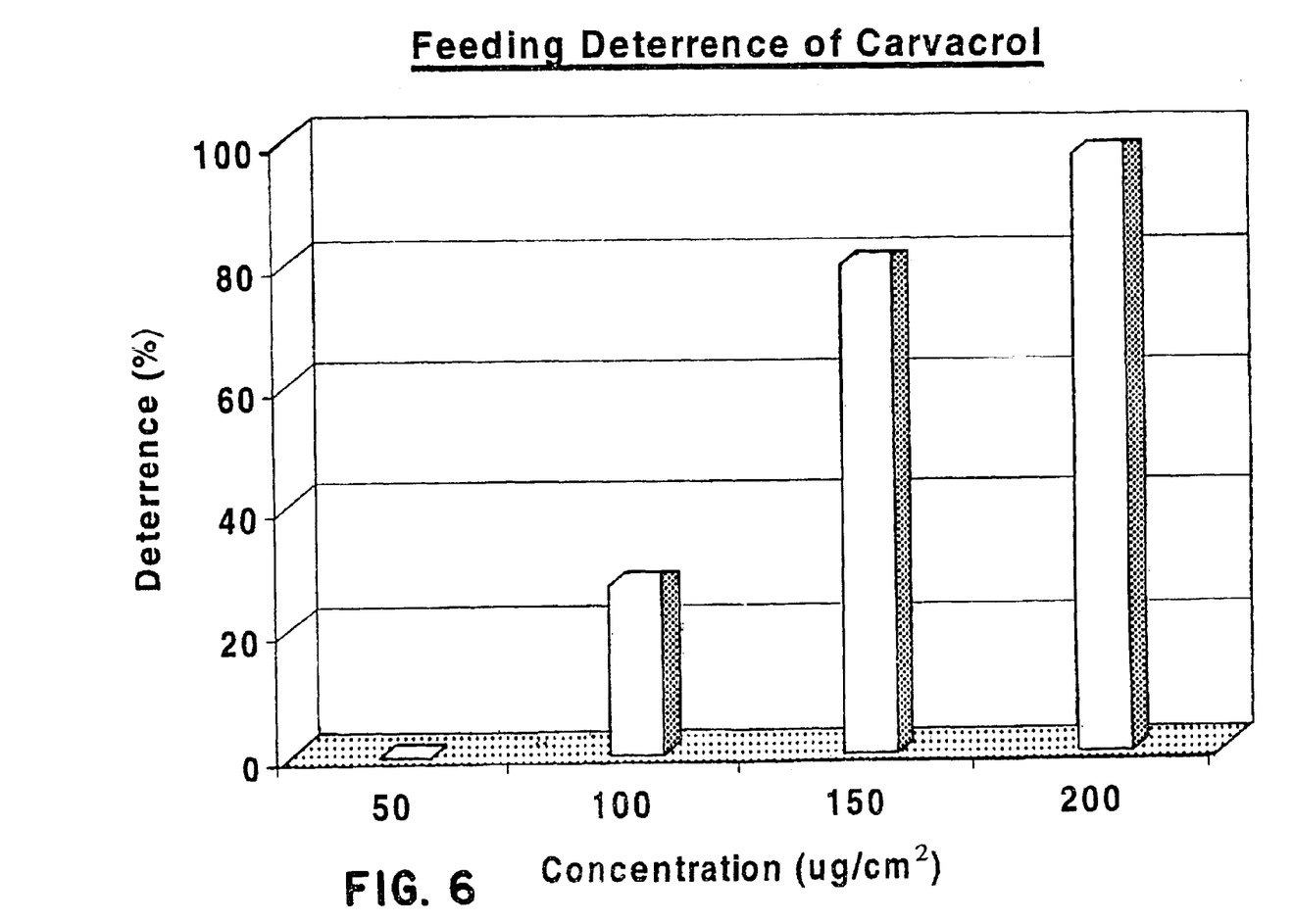
FIG. 6 is a graph of the feeding deterrence of carvacrol vs. larvae.

This data illustrates the unpredictability of a pesticide against different insects and larvae. PEP was found to be highly active against the cockroach but has less activity against the Asian armyworm. The 5-blend is active against both the cockroach and the Asian armyworm. The activity of thymol, even though a component of the 5-blend, is dependent on dilution. A further illustration of the variability in the effectiveness of various plant essential oils is shown in FIG. 5.

A bioassay similar to that for S. litura larvae was used for additional larvae. Cabbage leaf discs were dipped in emulsified aqueous solutions, diluted 1:200 in water, on which $2^{nd}$ instar green peach aphid nymphs were placed. For each treatment there was 10 aphids per disc with 5 replicates; each experiment was replicated in time (successive days) from 3–5 times. After 24 hours, aphids were reported as being (1) on the leaf disc and feeding; (2) alive, but walking off the disc; or (3) dead. In the field, aphids which cease feeding and abandon a host plant are very unlikely to survive. The test results are shown in Table 16.

TABLE 16

Pesticidal activity on green peach aphid nymphs.

| Treatment | Percentage of aphids | | |
|---|---|---|---|
| (n = 250) | Feeding | Walking (off disc) | Dead |
| Benzyl alcohol (BA) | 44.5 | 22.3 | 32.8 |
| 5-blend | 5.1 | 32.8 | 62.0 |
| BA + 5B (1:1) | 7.4 | 28.8 | 63.7 |
| Eugenol | 17.7 | 38.3 | 44.3 |
| Eugenol + 5B (1:1) | 9.1 | 48.6 | 42.6 |
| Control | 51.7 | 23.4 | 24.8 |

Benzyl alcohol is relatively inactive, eugenol is somewhat more active, and 5-blend is quite active at 1:200 dilution. Activity is manifest not only as mortality, but as feeding deterrence/repellency. Dilutions of 5-blend with either BA or eugenol are as effective as 5-blend alone with respect to feeding deterrence, and BA+5B mixture results in the same degree of mortality. A further set of experiments was conducted using PEP as a potential diluent for 5-blend as shown in Table 17.

TABLE 17

Pesticidal activity on green peach aphid nymphs.

| Treatment | Percentage of aphids | | |
|---|---|---|---|
| (n = 250) | Feeding | Walking (off disc) | Dead |
| 5-blend | 3.3 | 54.0 | 42.7 |
| Phenethyl propionate | 62.0 | 25.3 | 13.3 |
| 5B + PEP (1:1) | 16.7 | 49.3 | 35.3 |
| Control | 76.0 | 15.3 | 8.7 |

At this dilution, phenethyl propionate is essentially inactive. However dilution of 5-blend with PEP by 50% does not diminish the feeding deterrence or toxicity observed for 5-blend alone.

Tables 12–14, 16 and 17 provide data for 1:1 mixtures of the blend with the specifically identified compound. The 1:1 mixture has been shown to be effective but the mixtures are not limited thereto and other ratios may be used.

These results illustrate the effectiveness of the 5-blend as an effective pesticide for not only cockroaches and Asian armyworms, but also for green peach aphid nymphs. The 5-blend can be considered as a relatively broad spectrum pesticide. Phenethyl propionate shows much more specificity as a pesticide being highly effective against cockroaches, less toxic to Asian armyworms and only slightly toxic to green peach aphid nymphs. The effect of concentration of the pesticide is shown in FIG. 5 where a doubling in the concentration of carvacrol produces a 3–4 fold increase in deterrence of feeding.

Additional "cross walk" testing was conducted with eugenol. Table 18 provides data for 5% (by volume) eugenol in acetone and Table 19 provides data for 1% eugenol in acetone wherein five (5) American cockroaches were placed in the screened jars after the acetone had evaporated. IM=immobilized; KD=knockdown; D=dead; L=live (no effect).

TABLE 18

| Time | 5% Eugenol |
|---|---|
| 2 min | 1/5 IM |
| 5 min | 1/5 IM |
| 15 min | 3/5 IM |
| 30 min | 1/5 KD, 3/5 IM |
| 45 min | 1/5 KD, 3/5 IM |
| 1 hr. | 4/5 IM, 1/5 KD |
| 1.5 hr. | 4/5 IM, 1/5 KD |
| 2 hr. | 4/5 IM, 1/5 KD |
| 4 hr. | 4/5 D, 1/5 KD |
| 24 hr. | 5/5 D |

TABLE 19

| Time | 1% Eugenol |
|---|---|
| 2 min | 5/5 L |
| 5 min | 515 L |
| 15 min | 515 L |
| 30 min | 5/5 L |
| 45 min | 3/5 IM |
| 1 hr. | 1/5 KD, 3/5 IM |
| 1.5 hr. | 1/5 KD, 3/5 IM |
| 2 hr. | 1/5 KD, 3/5 IM |
| 4 hr. | 1/5 KD, 3/5 IM |
| 24 hr. | 2/5 IM (KD/IM recover) |

Table 20 provides data for 5% (by volume) eugenol in 95% Isopar M and Table 21 provides data for 1% (by volume) eugenol in 99% Isopar M. Isopar M is an isoparaffinic hydrocarbon sold by Exxon Corporation.

TABLE 20

| Time | 5% Eugenol |
|---|---|
| 2 min | 2/5 D, 1/5 IM |
| 5 min | 4/5 D, 1/5 IM |
| 10 min | 5/5 D |
| 15 min | — |

TABLE 21

| Time | 1% Eugenol |
|---|---|
| 2 min | 2/5 D, 1/5 KD, 1/5 IM |
| 5 min | 3/5 D, 1/5 IM |
| 15 min | 2/5 IM |
| 30 min | 2/5 IM |
| 45 min | 4/5 D, 1/5 IM |
| 1 hr. | 1/5 IM |
| 1.5 hr. | 5/5 D |

A control for 100% Isopar M is provided in Table 22.

TABLE 22

| Time | 100% Isopar M |
|---|---|
| 2 min | 2/5 D, 1/5 KD |
| 5 min | 3/5 D, 1/5 IM |
| 15 min | 2/5 KD |
| 30 min | 1/5 KD |
| 45 min | 2/5 KD |
| 1 hr. | 2/5 KD |
| 1.5 hr. | 2/5 KD |
| 2 hr. | 4/5 D, 1/5 KD |
| 4 hr. | 5/5 D |

The data shows that 5% eugenol is highly effective as a pesticide for American cockroaches in both modes of use.

In a further test, three (3) American cockroaches were placed in a screened jar containing 50 mg. of a dust formulation of which the following is typical.

| Phenyl ethyl propionate (PEP) | 4.50 |
|---|---|
| Eugenol | 1.75 |
| Methyl salicylate (MS) | 2.50 |
| * Microsorb 400 | 52.45 |
| NaHCO3 | 19.40 |
| CaCCO3 | 19.40 |

* A finely divided clay available from Englehart Industries.

The ratio of PEP to eugenol is approximately 2.5:1. The amount of liquid active ingredients may be increased. The Microsorb 400, sodium bicarbonate and calcium carbonate are present in sufficient amount to prepare a free-flowing dust even if increased amounts of PEP, eugenol and/or methyl salicylate are present. Table 23 provides data on the effects of the dust formulation on American cockroaches.

TABLE 23

| Time | IM | KD | Mortality |
|---|---|---|---|
| 1 hr. | 1/3 | — | — |
| 6 hr. | 1/3 | — | — |
| 24 hr. | — | — | 3/3 |

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method of killing cockroaches consisting of the steps of:

preparing eugenol in an isoparaffinic hydrocarbon solvent (Isopar), applying the eugenol in the hydrocarbon solvent to the cockroaches and the habitat thereof wherein the cockroaches are exposed to an effective dose of eugenol to kill the cockroaches.

2. The method of claim 1, wherein the eugenol is approximately 1% by volume and the balance is the hydrocarbon solvent.

3. The method of claim 2, wherein approximately 80% of the cockroaches are killed in 45 min.

4. A method of killing cockroaches consisting of the steps of:

preparing eugenol in an isoparaffinic hydrocarbon solvent (Isopar), applying the eugenol in the hydrocarbon solvent to the cockroaches and the habitat thereof wherein the cockroaches are exposed to an effective dose to kill the cockroaches, wherein the eugenol is approximately 5% by volume and the balance is the hydrocarbon solvent.

5. The method of claim 4, wherein approximately 100% of the cockroaches are killed in 10 min.

* * * * *